(12) United States Patent
Sukumaran et al.

(10) Patent No.: US 10,815,256 B2
(45) Date of Patent: Oct. 27, 2020

(54) DITHIOPHENE COMPOUND, PREPARATION AND ITS APPLICATION IN ORGANIC PHOTOVOLTAICS THEREOF

(71) Applicant: Council of Scientific and Industrial Research, Pune (IN)

(72) Inventors: Santosh Babu Sukumaran, Pune (IN); Vivek Chandrakant Wakchaure, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 48 days.

(21) Appl. No.: 16/317,087

(22) PCT Filed: Oct. 11, 2017

(86) PCT No.: PCT/IN2017/050464
§ 371 (c)(1),
(2) Date: Jan. 11, 2019

(87) PCT Pub. No.: WO2018/069935
PCT Pub. Date: Apr. 19, 2018

(65) Prior Publication Data
US 2019/0300554 A1 Oct. 3, 2019

(30) Foreign Application Priority Data

Oct. 11, 2016 (IN) .............................. 201611023587

(51) Int. Cl.
*C07F 7/22* (2006.01)
*C08G 61/12* (2006.01)
*C07D 495/04* (2006.01)
*H01L 51/00* (2006.01)
*C07D 519/00* (2006.01)
*H01L 51/42* (2006.01)

(52) U.S. Cl.
CPC .......... *C07F 7/2208* (2013.01); *C07D 495/04* (2013.01); *C07D 519/00* (2013.01); *C08G 61/126* (2013.01); *H01L 51/0036* (2013.01); *H01L 51/0043* (2013.01); *H01L 51/0068* (2013.01); *H01L 51/0074* (2013.01); *C08G 2261/12* (2013.01); *C08G 2261/149* (2013.01); *C08G 2261/3243* (2013.01); *C08G 2261/91* (2013.01); *C08G 2261/92* (2013.01); *H01L 51/4253* (2013.01)

(58) Field of Classification Search
CPC ............................. C08G 61/126; C07F 7/2208
See application file for complete search history.

(56) References Cited

FOREIGN PATENT DOCUMENTS

KR    20160004923    1/2016

OTHER PUBLICATIONS

European Patent Office, International Search Report for PCT/IN2017/050464 dated Feb. 5, 2018.
Kularatne et al., "Structural variation of donor-acceptor copolymers containing benzodithiophene with bithienyl substituents to achieve high open circuit voltage in bulk heterojunction solar cells", Journal of Materials Chemistry A: Materials for Energy and Sustainability, 1(48);15535-15543, Jan. 1, 2013.
Written Opinion for International Application No. PCT/IN2017/050464 dated Feb. 5, 2018.
Wu et al., "Covalently Bound Clusters of Alpha-Substituted PDI-Rival Electron Acceptors to Fullerene for Organic Solar Cells", Journal of the American Chem. Society, 138(23):7248-7251, Jun. 1, 2016.

*Primary Examiner* — Wenwen Cai
(74) *Attorney, Agent, or Firm* — Fish & Richardson P.C.

(57) ABSTRACT

The present invention disclosed a novel (4,8-bis(5-(trimethylstannyl)thiophen-2-yl)benzo[1,2-b:4,5-b']dithiophene-2,6-diyl)bis(trimethylstannane) compound, its preparation and use for the synthesis of polymers, which is used to build devices for capacitor and solar applications. The present invention further discloses to an improved process for the synthesis of DTBDT having improved yields.

10 Claims, 6 Drawing Sheets

DITHIOPHENE COMPOUND, PREPARATION AND ITS APPLICATION IN ORGANIC PHOTOVOLTAICS THEREOF

FIELD OF THE INVENTION

The present invention relates to a novel compound of formula (I), its preparation and its use for the synthesis of polymers of formula (II), which is used to build devices for capacitor and solar applications. The present invention further relates to an improved process for the synthesis of DTBDT having improved yields.

BACKGROUND AND PRIOR ART

Organic materials such as conjugated polymers, which are extended for electron donor possibilities for solar cells, transistors and so on are being developed. Here a 2d polymerized sheet is developed and it is expected to have enhanced electron donor capabilities. Its characterization is under progress and advanced studies are in progress, data expected in about two weeks. Further, one derivative of the 2d polymer also synthesized. Device fabrication will be done shortly.

Article titled, "Direct access to 4,8-functionalized benzo[1,2-b:4,5-b'] dithiophenes with deep low-lying HOMO levels and high mobilities" by Tang, W. et al. in *J. Mater. Chem. A* 2, 13580-13586 (2014) reports a general methodology has been proposed for the straightforward access to 4,8-functionalized benzo[1,2-b:4,5-b']dithiophenes (BDTs) via Pd mediated coupling reactions including Suzuki-Sonogashira coupling and carbon-sulfur bond formation reactions. This versatile platform can be used to construct a library of BDT core centred conjugated systems, featuring large fused-ring structure and good charge mobility, where a hole mobility of 0.061 $cm^2\ V^{-1}\ s^{-1}$ is demonstrated. With the energy level fine-tuned with functionalization, the charge transporting BDTs show great potential for donor-acceptor polymers.

Article titled "Donor-Acceptor semiconducting polymers containing benzodithiophene with bithienyl substituents" by E Zhu et al. published in *J. Mater. Chem. A*, 2014, 2, pp 13580-13586 reports synthesis and photovoltaic properties of two donor-acceptor polymers containing benzodithiophene with 3,3',5-trihexylbithienyl substituents are reported. Benzo[c][1,2,5]thiadiazole and 5-hexylthieno[3,4-c]pyrrole-4,6-dione were used as acceptor building blocks for the synthesis of donor-acceptor polymers.

Article titled "Highly conjugated side-chain-substituted Benzo[1,2-b:4,5-b']dithiophene-based conjugated polymers for use in polymer solar cells" by HS Chung et al. published in *Macromolecules*, 2014, 47 (1), pp 97-105 reports a series of novel benzo[1,2-b:4,5-b']dithiophene (BDT)-based conjugated polymers synthesized using a Stille cross-coupling reaction. These polymers contained dithienyl thieno[3,4-c]pyrrole-4,6-dione (DTTPD) as an acceptor. Alkylthienylenevinylene thiophene side groups were introduced into the BDT units, and the solubility, absorption spectra, energy levels, charge transport, blend film morphology, and photovoltaic properties of the resulting polymer (poly[4,8-bis{2, 2'-(5-ethylhexyl)thienylenevinylenethiophene}benzo[1,2-b; 3,4-b]dithiophene-2,6-diyl-alt-1,3-di(thien-5'-yl)-5-octyldodecyl[3,4-c]pyrrole-4,6-dione-2,2'-diyl], PBDTTVT-DTTPD) are reported.

Article titled "Systematic investigation of benzodithiophene- and diketopyrrolopyrrole-based low-bandgap polymers designed for single junction and tandem polymer solar cells" by L Dou et al. published in *J. Am. Chem. Soc.*, 2012, 134 (24), pp 10071-10079 reports the design, synthesis, and characterization of a series of new low bandgap polymers specifically for tandem polymer solar cells. These polymers have a backbone based on the benzodithiophene (BDT) and diketopyrrolopyrrole (DPP) units. Alkylthienyl and alkylphenyl moieties were incorporated onto the BDT unit to form BDTT and BDTP units, respectively.

Article titled "New alkoxylphenyl substituted benzo[1,2-b:4,5-b'] dithiophene-based polymers: synthesis and application in solar cells" by J Yuan et al. published in *J. Mater. Chem. A*, 2013, 1, 10639-10645 reports synthesis of two new alkoxylphenyl substituted benzo[1,2-b:4,5-b']dithiophene (BDTPO)-based polymers (PBDTPO-DTBO and PBDTPO-DTBT). UV-Vis absorption spectra of the polymers show broad and strong absorption bands from 300-750 nm both in $CHCl_3$ solutions and films.

Article titled "Bandgap and Molecular Energy Level Control of Conjugated Polymer Photovoltaic Materials Based on Benzo[1,2-b:4,5-b']dithiophene" by J Hou et al. published in *Macromolecules*, 2008, 41 (16), pp 6012-6018 reports synthesis of benzo[1,2-b:4,5-b']dithiophene (BDT) with different conjugated units and their photovoltaic performance. Eight new BDT-based polymers with commonly used conjugated units, including thiophene, benzo[c][1,2,5] thiadiazole (BT), thieno[3,4-b]pyrazine (TPZ), etc., are synthesized.

Article titled "Synthesis and Photovoltaic Performances of Benzo[1,2-b:4,5-b']dithiophene-alt-2,3-diphenylquinoxaline Copolymers Pending Functional Groups in Phenyl Ring" by H Tan et al. published in *Journal of Polymer Science, Part A: Polymer Chemistry*; 2013, 51, pp 1051-1057 reports Two donor/acceptor (D/A)-based benzo[1,2-b:4,5-b']dithiophene-alt-2,3-biphenyl quinoxaline copolymers of P1 and P2 synthesized with pending different functional groups (thiophene or triphenylamine) in the 4-positions of phenyl rings. Their thermal, photophysical, electrochemical, and photovoltaic properties, as well as morphology of their blending films were investigated.

Article titled "Structural variation of donor-acceptor copolymers containing benzodithiophene with bithienyl substituents to achieve high open circuit voltage in bulk heterojunction solar cells" by R S Kularatne et al. published in *J. Mater. Chem. A*, 2013, 1, pp 15535-15543 reports three new donor-acceptor copolymers P1, P2, and P3 synthesized with benzodithiophene with bithienyl substituents as the donor and 5,6-difluorobenzo[c][1,2,5]thiadiazole, 4,7-di (thiophen-2-yl)benzo[c][1,2,5]thiadiazole, and 5,6-difluoro-4,7-di(thiophen-2-yl)benzo[c][1,2,5]thiadiazole as the acceptors, respectively.

Article titled "Benzo[1,2-b:4,5-b']dithiophene and Thieno [3,4-c]pyrrole-4,6-dione Based Donor-π-Acceptor Conjugated Polymers for High Performance Solar Cells by Rational Structure Modulation" by S Liu et al. published in *Macromolecules*, 2015, 48 (9), pp 2948-2957 reports a series of benzo[1,2-b:4,5-b']dithiophene and thieno[3,4-c]pyrrole-4,6-dione (BDT-TPD) based copolymers (P1-P4) with D-π-A structures. When the it bridges change from 2,2'-bithiophene to thieno[3,2-b]thiophene and then to 3-hexylthieno[3,2-b]thiophene, the performance of the polymer photovoltaic devices shows significant improvement.

Article titled "Thieno[3,2-b]thiophene-Substituted Benzo [1,2-b:4,5-b']dithiophene as a Promising Building Block for Low Bandgap Semiconducting Polymers for High-Performance Single and Tandem Organic Photovoltaic Cells" by J H Kim et al. published in *Chem. Mater.*, 2014, 26 (2), pp 1234-1242 reports a new poly {4,8-bis((2-ethylhexyl)thieno

[3,2-b]thiophene)-benzo[1,2-b:4,5-b']dithiophene-alt-2-ethylhexyl-4,6-dibromo-3-fluorothieno[3,4-b]thiophene-2-carboxylate} (PTTBDT-FTT) comprising bis(2-ethylhexylthieno[3,2-b]thiophenylbenzo[1,2-b:4,5-b'] dithiophene (TTBDT) and 2-ethylhexyl 3-fluorothieno[3,4-b]thiophene-2-carboxylate (FTT).

Article titled "Correlation of Structure and Photovoltaic Performance of Benzo[1,2-b:4,5-b']dithiophene Copolymers Alternating with Different Acceptors" by J Yu et al. published in *New Journal of Chemistry;* 2015; 39(3); pp 2248-2255 reports four p-conjugated benzo[1,2-b:4,5-b0]dithiophene (BDT) based polymers synthesized for application in polymer solar cells. These polymers possessed desirable HOMO/LUMO levels for polymer photovoltaic applications. PBDTT-TTz and PBDTT-DTBT displayed strong absorption in the range of 300-650 nm, while PBDTT-DPP and PBDTT-TTDPP showed a further 100 nm extended absorption band.

Article titled "Side-chain manipulation on accepting units of two-dimensional benzo[1,2-b:4,5-b']dithiophene polymers for organic photovoltaics" by Z Xu et al. published in *Polym. Chem.*, 2016, 7, 1486-1493 reports Two donor-acceptor alternating polymers of bis(octylthio)thienyl benzo [1,2-b:4,5-b']dithiophene (BDTTs) and fluorinated benzo[c] [1,2,5]thiadiazole (fBT) or 5-dodecylthienyl-6-fluorobenzo [c][1,2,5]thiadiazole designed for organic photovoltaic applications.

Article titled "Side-chain Engineering of Benzo[1,2-b:4,5-b']dithiophene Core-structured Small Molecules for High-Performance Organic Solar Cells" by X Yin *Sci Rep.;* 2016 May 3; 6; pp 25355 reports three novel small molecules developed by side-chain engineering on benzo[1,2-b:4,5-b'] dithiophene (BDT) core. The typical acceptor-donor-acceptor (A-D-A) structure is adopted with 4,8-functionalized BDT moieties as core, dioctylterthiophene as π bridge and 3-ethylrhodanine as electron-withdrawing end group.

Article titled "Enhanced Photovoltaic Performance by Modulating Surface Composition in Bulk Heterojunction Polymer Solar Cells Based on PBDTTT-C-T/PC$_{71}$BM" by X Guo et al. published in *Adv. Mater.* 2014, 26, 4043-4049 reports the conventional structure and inverted structure PSCs based on PBDTTT-C-T/PC 71 BM as the model system without or with the use of solvent additive DIO.

Benzo[1,2-b:4,5-b0]dithiophene (BDT) has been proved to be one of the most important fused-ring structured building blocks in the design of conjugated polymer donors. BDT has shown high mobility and lower highest occupied molecular orbital (HOMO) level. This type of donor molecule in conjugation with suitable electron acceptor molecules is very much useful for bulk heterojunction (BHJ) solar cells. The BDT derived polymers were first developed as donors for BHJ solar cells by Hou et al. in 2008. (*Macromolecules,* 2008, 41, 6012). A large spectrum of BDT derived donors have been developed since then by introducing various substituents including alkyl, alkylthienyl, and alkyl phenylethynyl to the benzene core of BDT. Here we are reporting thiophene substituent with free second position to the benzene core of BDT.

There are many covalent organic polymers but all are insoluble so it is impossible to use those in devices application so there is a need to developed 2D material with solubility, further the covalent organic polymers find applications in organic photovoltaics (*Angewandte Chemie International Edition,* 2008, 47: 8826-8830, *Chem. Eur. J.,* 2014;

20: 14614-14618). Therefore, it is the need to develop novel compounds which has application in organic photovoltaics.

OBJECTIVE OF THE INVENTION

The main objective of the present invention is to provide a novel compound of formula (I) and process for preparation thereof.

Another objective of the present invention is to provide novel compound of formula (II) which is used to build devices for capacitor and solar applications and process for preparation thereof.

Yet another objective of the present invention is to provide an improved process for the synthesis of 4,8-di(thiophen-2-yl)benzo[1,2-b:4,5-b']dithiophene with high yields.

SUMMARY OF THE INVENTION

Accordingly, the present invention provides a novel compound of formula (I);

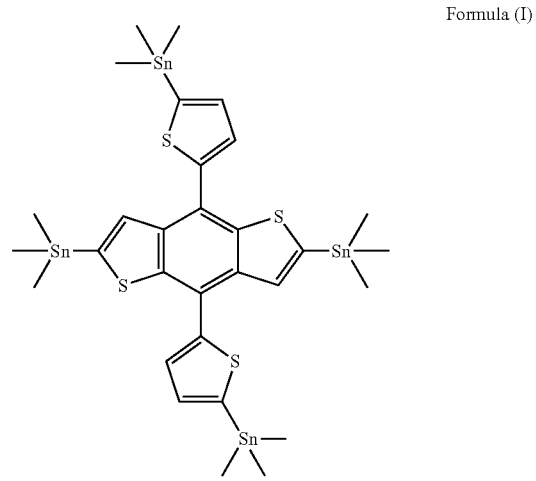

Formula (I)

In preferred embodiment, said compound of formula (I) is (4,8-bis(5-(trimethylstannyl)thiophen-2-yl)benzo[1,2-b:4,5-b']dithiophene-2,6-diyl)bis(trimethylstannane).

In another embodiment, the present invention provides a process for the synthesis of compound of formula (I), wherein said process comprises the steps of:

a) Adding t-butyl lithium to a solution of 4,8-di(thiophen-2-yl)benzo[1,2-b:4,5-b']dithiophene in solvent to obtain the reaction mixture;

b) Adding trimethyltin chloride in solvent to the reaction mixture of step (a) followed by work-up and purification to afford desired compound of formula (I).

In preferred embodiment, said solvent is Tetrahydrofuran (THF).

In another embodiment, the present invention provides a novel 2D soluble organic covalent polymer of formula (II);

Formula (II)

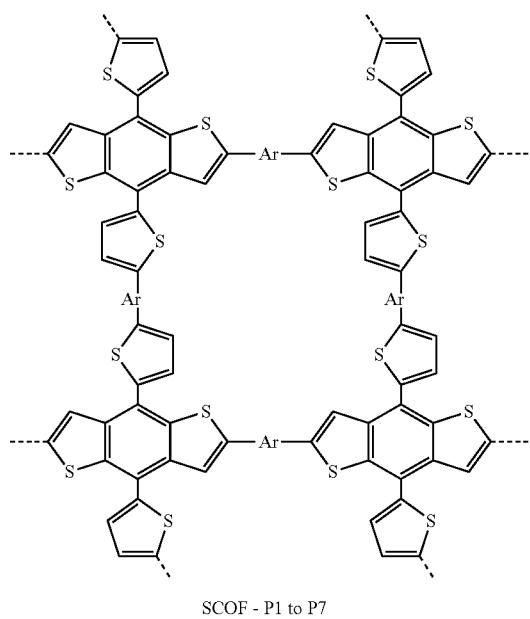

SCOF - P1 to P7

Wherein;

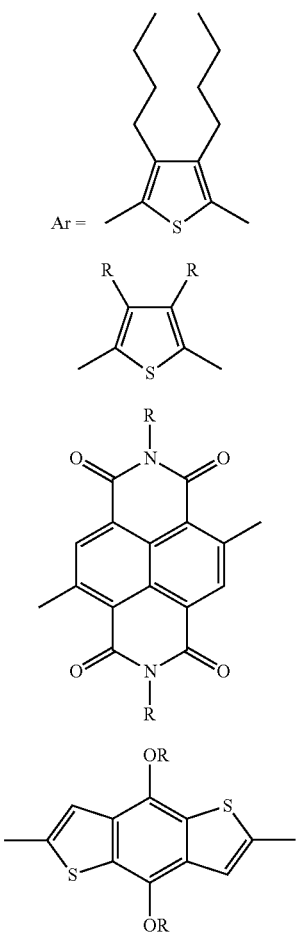

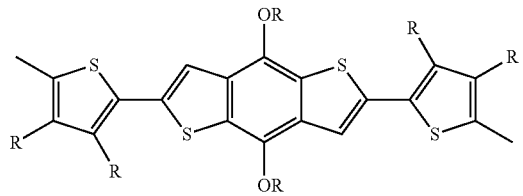

S4

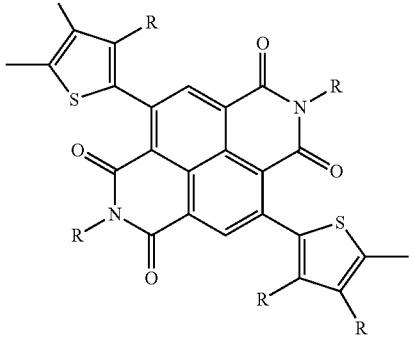

S5

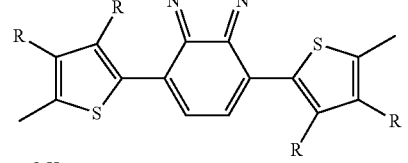

S7

R = 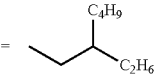

In preferred embodiment, said compound of formula (II) is selected from SCOF P1 to P7.

In still another embodiment, the present invention provides a process for the synthesis of polymer of formula (II), wherein said process comprises the steps of:

a) Dissolving monomer of formula (I) and Br—Ar—Br in solvent to obtain the reaction mixture;
b) Degassing the solution of step (a) and adding Pd(PPh$_3$)$_4$ followed by heating the reaction mixture at a temperature in the range of 100 to 110° C. for the period in the range of 70 to 74 hrs;
c) Adding 2-bromothiophene and trimethyl(thiophen-2-yl) stannane followed by heating the reaction mixture at a temperature in the range of 100 to 110° C. for the period in the range of 10 to 14 hrs.

In preferred embodiment, said solvent is Toluene.

In another preferred embodiment, said Ar is selected from

S1

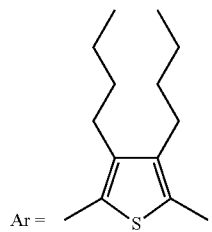

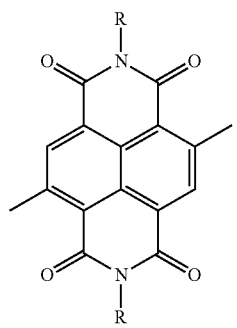

S3

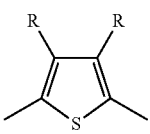

S6

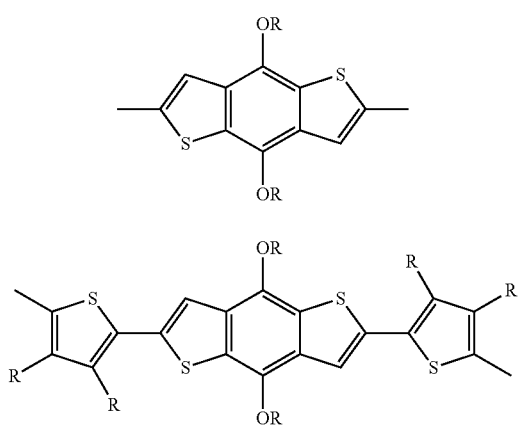

S2

S4

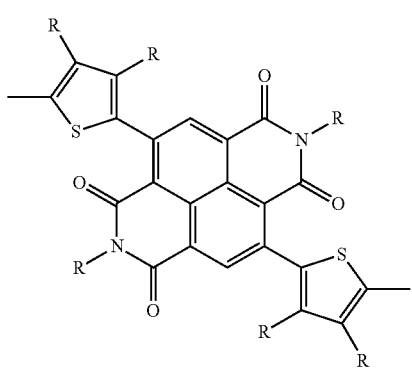

S5

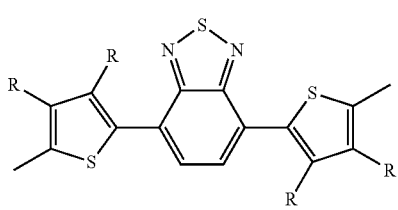

S7

In one embodiment, the present invention provides a one pot gram scale synthesis of 4,8-di(thiophen-2-yl) benzo[1,2-b:4,5-b']dithiophene (DTBDT) by using simple well known Grignard reaction. The compound is useful to synthesize monomers, which are then polymerized and used to build useful devices for various applications.

In preferred embodiment, the present invention provides a one pot process for the synthesis of 4,8-di(thiophen-2-yl) benzo[1,2-b:4,5-b']dithiophene (DTBDT) comprising the steps of:

a) Adding a solution of 2-bromothiophene in solvent to a suspension of magnesium and iodine in solvent at 0° C. followed by refluxing for the period in the range of 1 to 2 hr;

b) Adding 4,8-dehydrobenzo [1,2-b:4,5-b'] dithiophene-4,8-dione to the reaction mixture of step (a) followed by stirring reaction mixture at a temperature in the range of 50 to 60° C. for the period in the range of 5 to 7 hours;

c) Cooling the mixture of step (b) to a temperature at 25° C. and adding a solution of tin chloride in HCl followed by stirring for the period in the range of 1 to 2 hours to afford 4,8-di(thiophen-2-yl) benzo [1,2-b:4,5-b']dithiophene (DTBDT).

In preferred embodiment, said solvent is tetrahydrofuran (THF).

DETAILED DESCRIPTION OF THE INVENTION

The invention will now be described in detail in connection with certain preferred and optional embodiments, so that various aspects thereof may be more fully understood and appreciated.

In view of above, the present invention provides a novel dithiophene compound, preparation and its application in organic photovoltaics thereof.

In an embodiment, the present invention provides a novel compound of formula (I);

Formula (I)

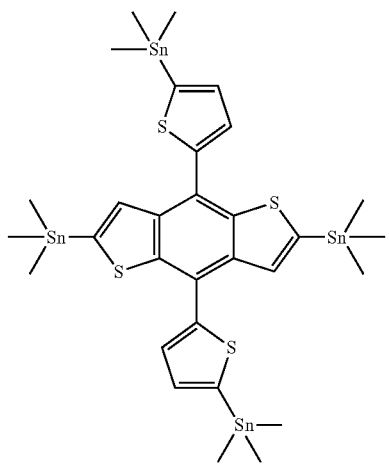

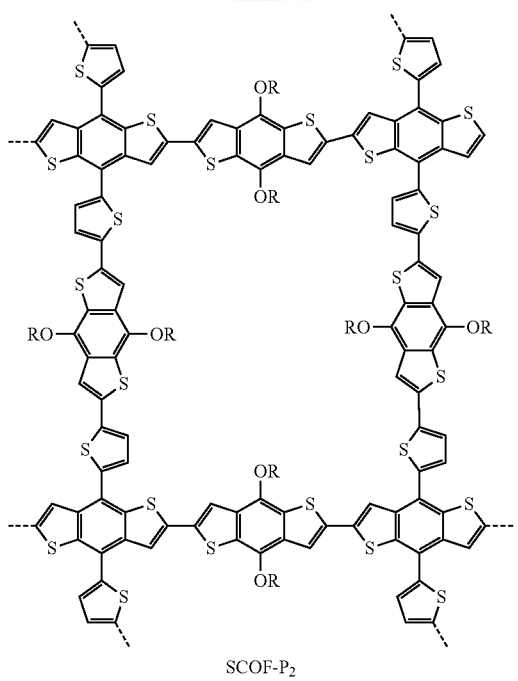

SCOF-P₂

In preferred embodiment, said compound of formula (I) is (4,8-bis(5-(trimethylstannyl)thiophen-2-yl)benzo[1,2-b:4,5-b']dithiophene-2,6-diyl)bis(trimethylstannane).

In another embodiment, the present invention provides a process for the synthesis of compound of formula (I), wherein said process comprises the step of:
  a) Adding t-butyl lithium to a solution of 4,8-di(thiophen-2-yl)benzo[1,2-b:4,5-b']dithiophene in solvent to obtain the reaction mixture;
  b) Adding trimethyltin chloride in solvent to the reaction mixture of step (a) followed by work-up and purification to afford desired compound of formula (I).

In preferred embodiment, said solvent is Tetrahydrofuran (THF).

In another embodiment, the present invention provides a novel 2D soluble organic covalent polymer of formula (II);

In preferred embodiment, said compound of formula (II) is selected from SCOF P1 to P7.

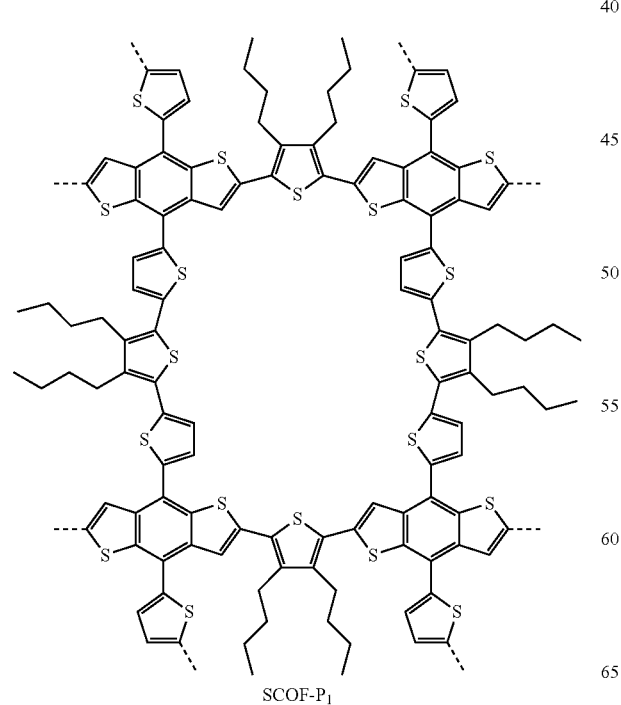

SCOF-P₁

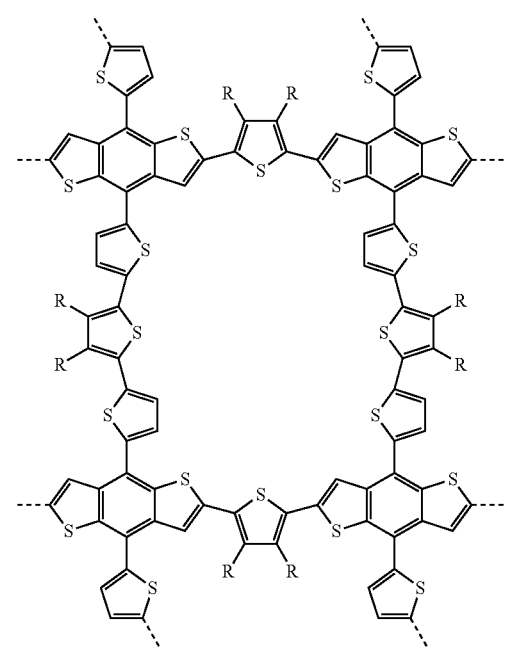

SCOF-P₃

-continued

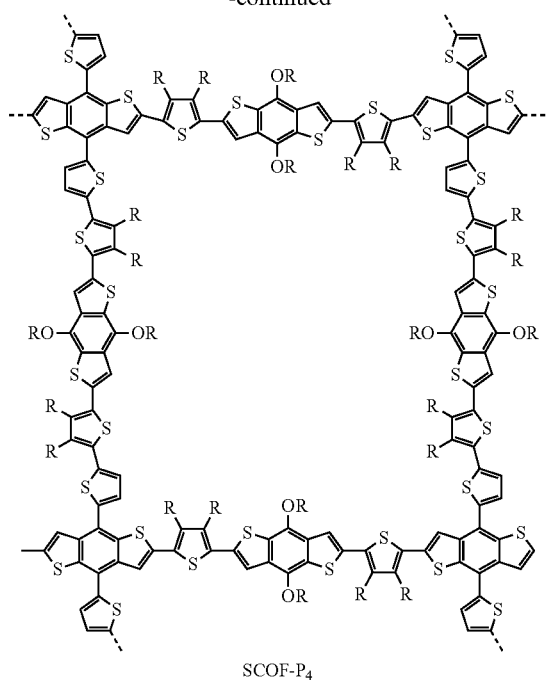

SCOF-P₄

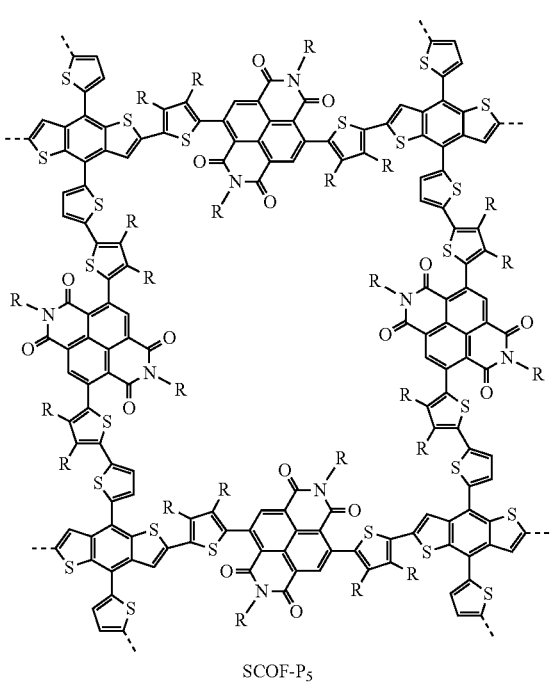

SCOF-P₅

-continued

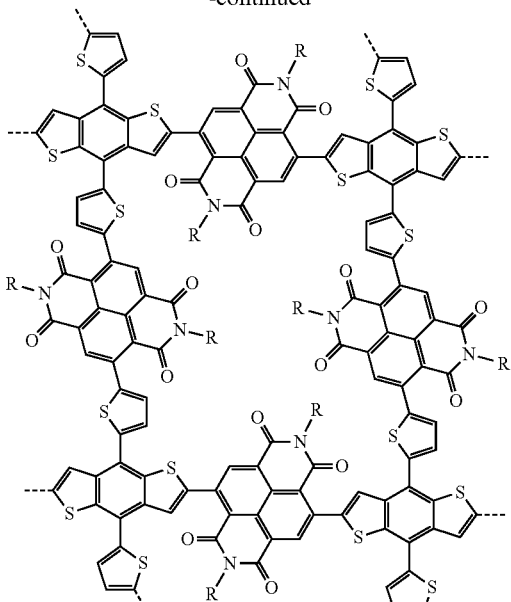

SCOF-P₆

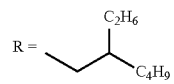

SCOF-P₇

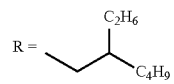

In still another embodiment, the present invention provides a process for the synthesis of polymer of formula (II), wherein said process comprises the steps of:

a) Dissolving monomer of formula (I) and Br—Ar—Br in solvent to obtain the reaction mixture;
b) Degassing the solution of step (a) and adding Pd(PPh3)4 followed by heating the reaction mixture at temperature in the range of 100 to 110° C. for the period in the range of 70 to 74 hrs;
c) Adding 2-bromothiophene and trimethyl(thiophen-2-yl)stannane followed by heating the reaction mixture at temperature in the range of 100 to 110° C. for the period in the range of 10 to 14 hrs.

In preferred embodiment, said solvent is Toluene.

The above process for synthesis of compound and its polymer is shown below in Scheme A:

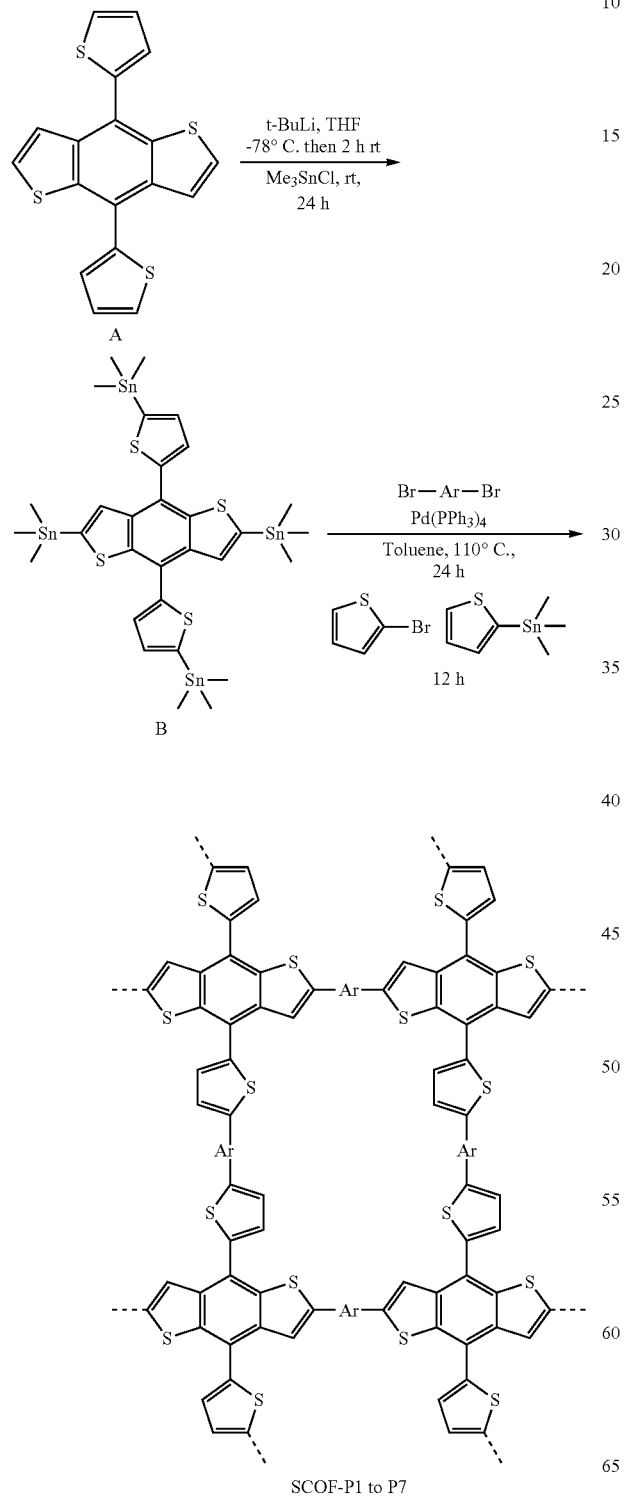

SCOF-P1 to P7

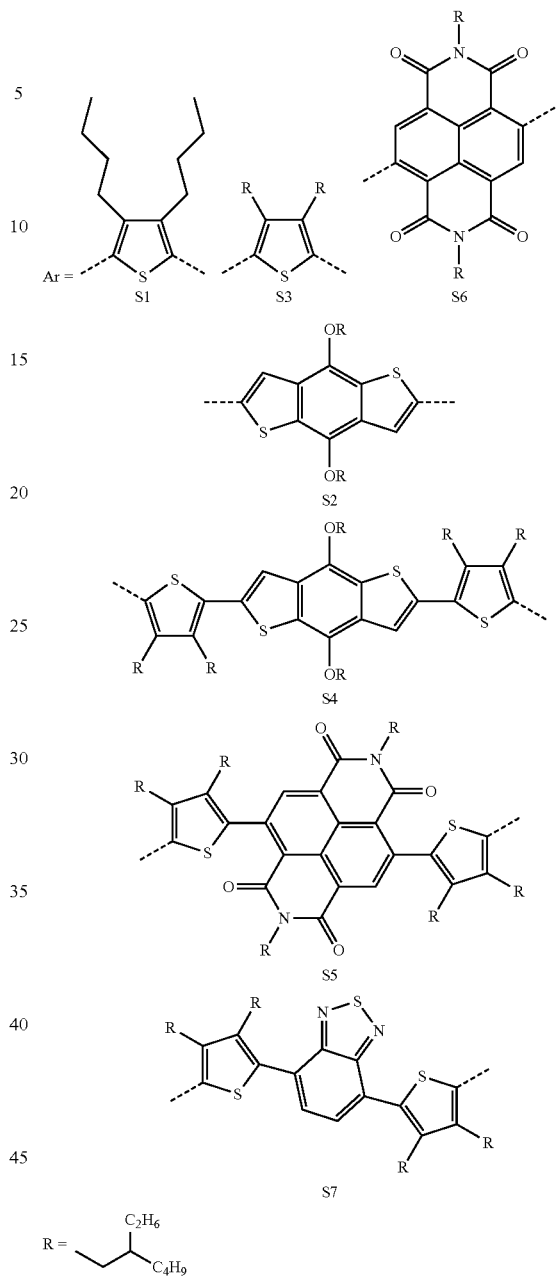

Figure 1:
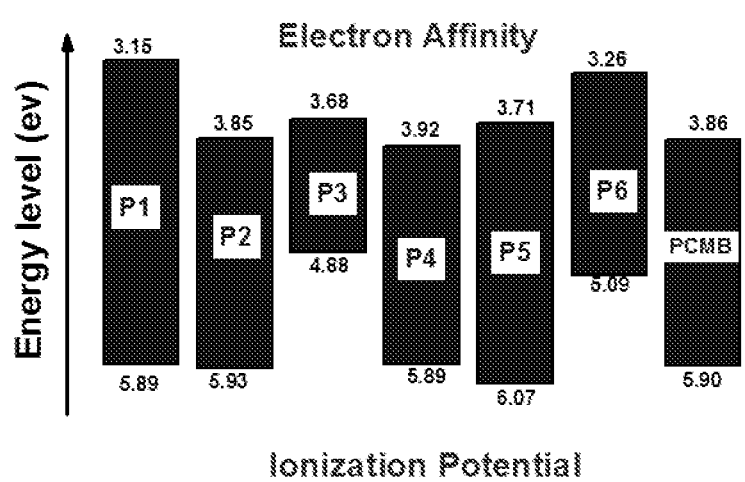
FIG. 1: depicts Energy Level Diagram of Polymers (from CV).
Figure 2:
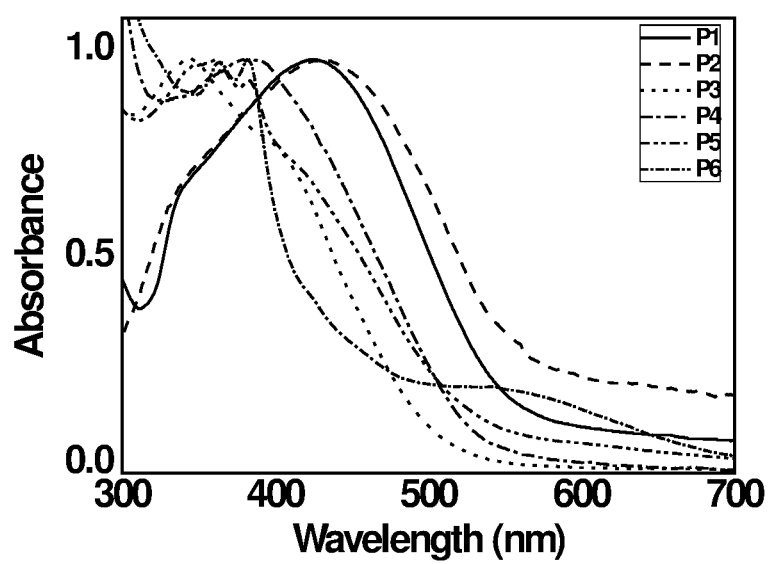
FIG. 2: depicts Normalized Absorbance Spectra of Polymers (in DCM).
Figure 3:
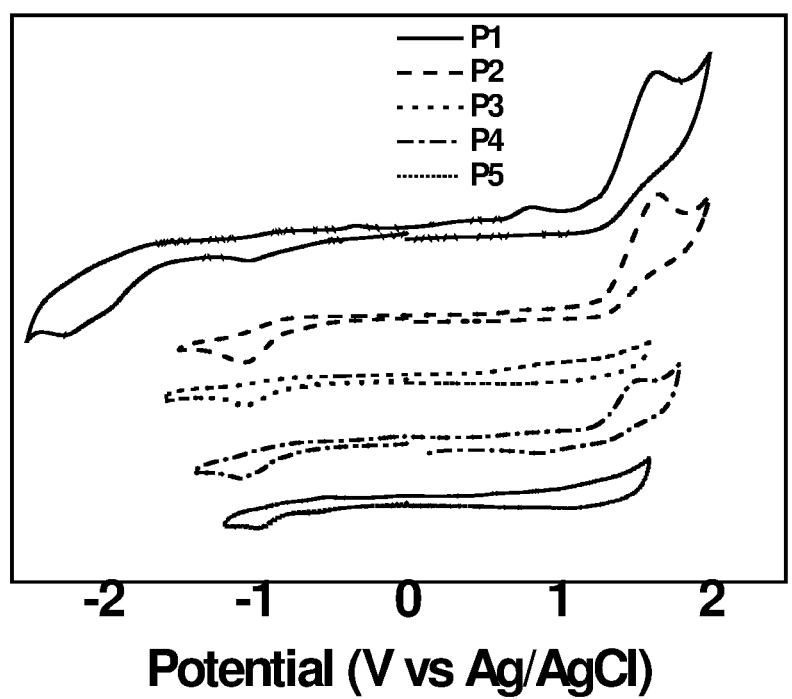
FIG. 3: depicts cyclic voltammograms of the films of the polymers on a Pt electrode in acetonitrile solution containing 0.1M $Bu_4NPF_6$ at a scan rate of 50 $mV/s^{-1}$.
Figure 4:
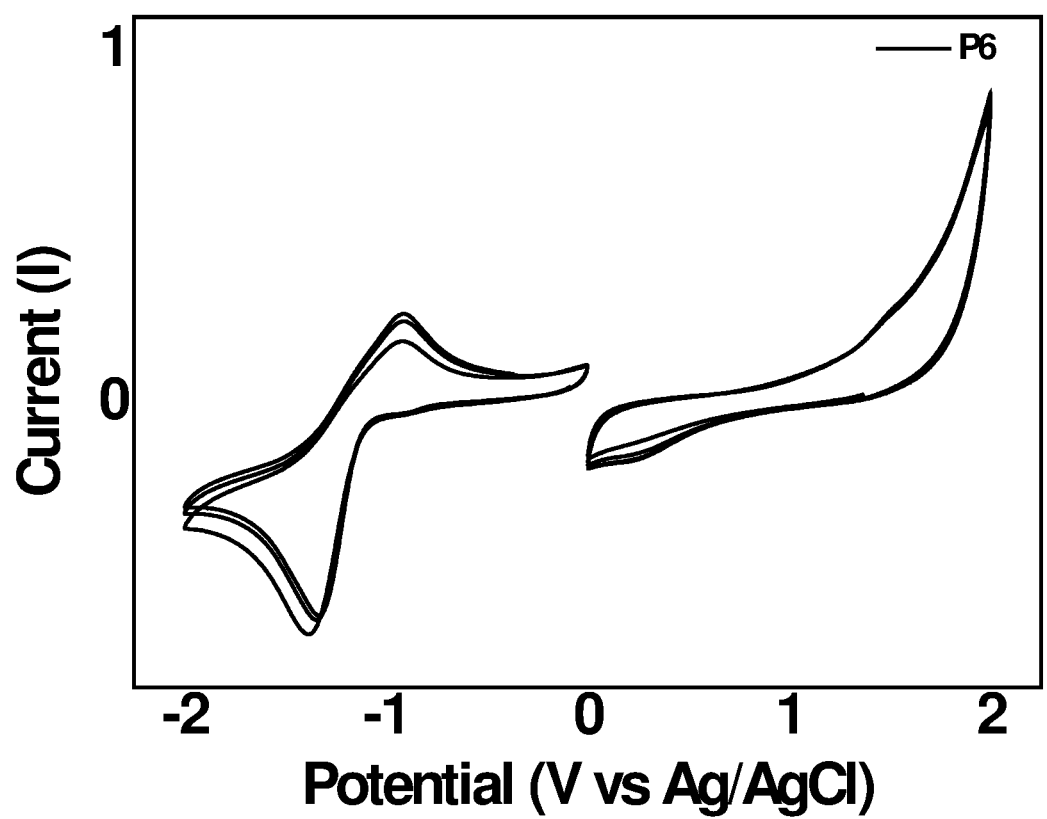
FIG. 4: depicts cyclic voltammograms of the films of the P6 on a Pt electrode in acetonitrile solution containing 0.1M $Bu_4NPF_6$ at a scan rate of 50 $mV/s^{-1}$.
Figure 5:
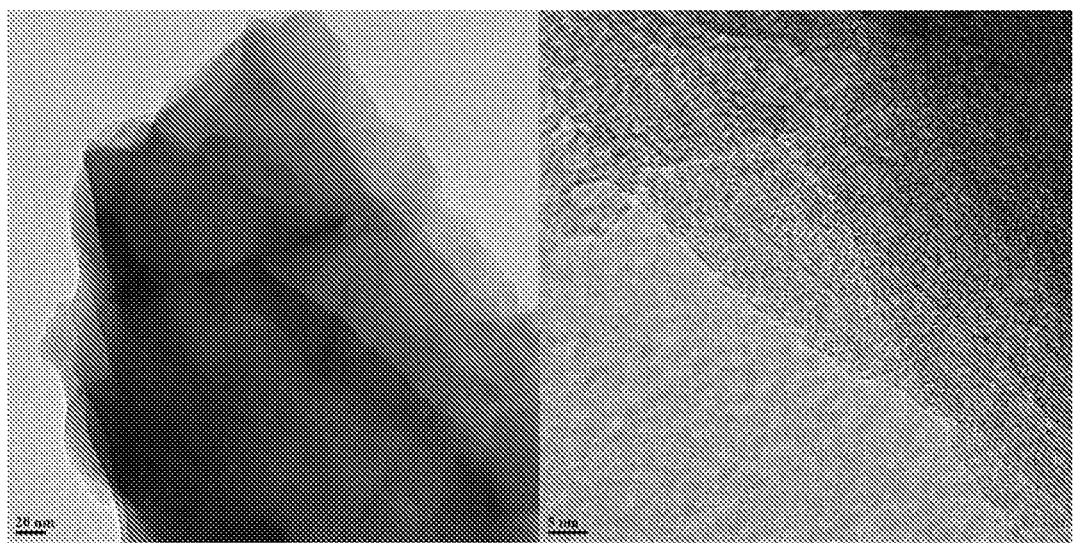
FIG. 5: depicts TEM images of Polymer 4.
Figure 6:
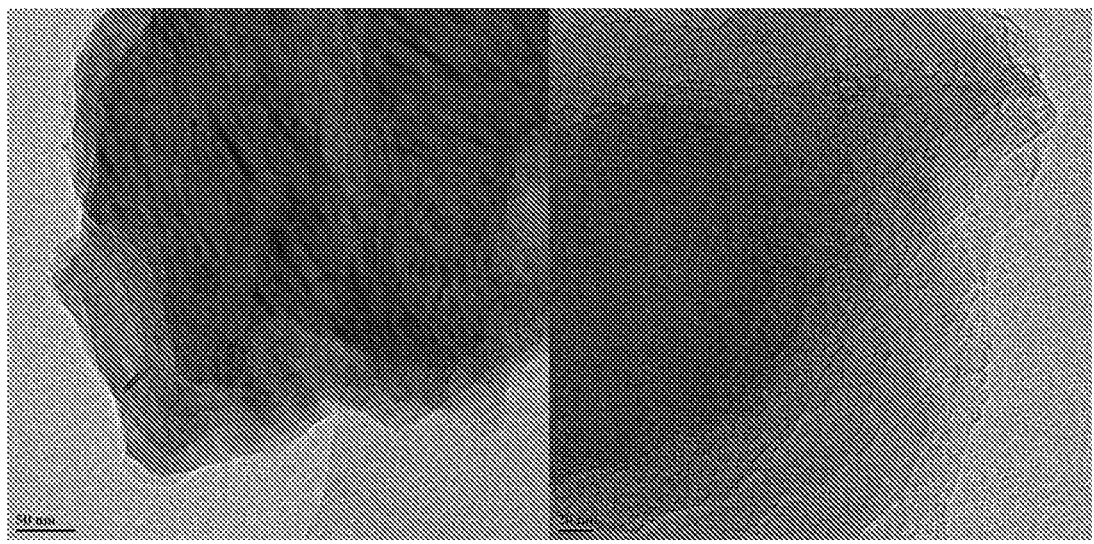
FIG. 6: depicts TEM images of Polymer 5.

In an aspect, the present invention provides the characterization data of synthesized polymers wherein FIG. 1 represents Energy Level Diagram of Polymers (from CV); FIG. 2 represents Normalised Absorbance Spetra of Polymers (in DCM); FIG. 3 shows the cyclic voltammograms of the films of the polymers on a Pt electrode in acetonitrile solution containing 0.1M $Bu_4NPF_6$ at a scan rate of 50 mV/s$^{-1}$; FIG. 4 shows the cyclic voltammograms of the films of the P6 on a Pt electrode in acetonitrile solution containing 0.1M $Bu_4NPF_6$ at a scan rate of 50 mV/s$^{-1}$; FIGS. 5 and 6 shows the TEM images of Polymer 4 and Polymer 5 respectively.

In another aspect, the present invention provides the electrochemical and optical properties of synthesized polymers as shown below in Table 1.

TABLE 1

| Polymer | HOMO (ev) | LUMO (ev) | $E_g$ (ev) | $\lambda_{max}$ (nm) | $\lambda_{onset}$ (nm) | $E_g$ (from UV) (ev) |
|---|---|---|---|---|---|---|
| P1 | 5.89 | 3.15 | 2.74 | 427 | 549 | 2.26 |
| P2 | 5.93 | 3.85 | 2.08 | 429 | 557 | 2.23 |
| P3 | 4.88 | 3.68 | 1.2 | 343 | 502 | 2.47 |
| P4 | 5.89 | 3.92 | 1.97 | 379 | 530 | 2.34 |
| P5 | 6.07 | 3.71 | 2.36 | 361 | 527 | 2.36 |
| P6 | 5.09 | 3.26 | 1.83 | 382 | 680 | 1.83 |

In one embodiment, the present invention provides a one pot gram scale synthesis of 4,8-di(thiophen-2-yl)benzo[1,2-b:4,5-b']dithiophene (DTBDT) by using simple well known Grignard reaction. The compound is useful to synthesize monomers, which are then polymerized and used to build useful devices for various applications.

In preferred embodiment, the present invention provides a one pot process for the synthesis of 4,8-di(thiophen-2-yl)benzo[1,2-b:4,5-b']dithiophene (DTBDT) comprising the steps of:
a) Adding a solution of 2-bromothiophene in solvent to a suspension of magnesium and iodine in solvent at 0° C. followed by refluxing for the period in the range of 1 to 2 hr;
b) Adding 4,8-dehydrobenzo[1,2-b:4,5-b']dithiophene-4,8-dione to the reaction mixture of step (a) followed by stirring reaction mixture at temperature in the range of 50 to 60° C. for the period in the range of 5 to 7 hours;
c) Cooling the mixture of step (b) to temperature at 25° C. and adding a solution of tin chloride in HCl followed by stirring in the range of 1 to 2 hours to afford 4,8-di(thiophen-2-yl)benzo[1,2-b:4,5-b']dithiophene (DTBDT).

In preferred embodiment, said solvent is tetrahydrofuran (THF).

The process for the synthesis of 4,8-di(thiophen-2-yl)benzo[1,2-b:4,5-b']dithiophene (DTBDT) by using simple well known Grignard reaction is as depicted in scheme 2:

Scheme 2: Synthetic Procedure of DTBDT

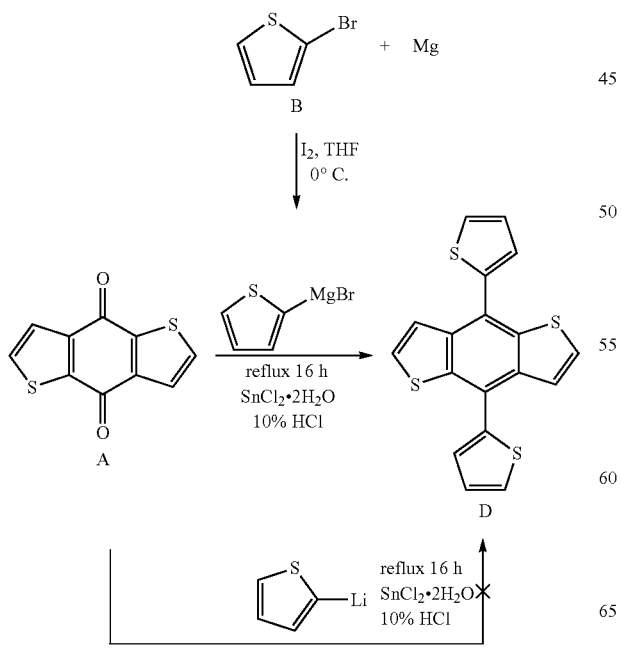

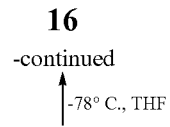

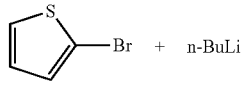

The process disclosed herein leads to over 40% yield of the desired product.

In a preferred embodiment, the process yields over 60% of DTBDT.

The compound synthesized, DTBDT, was characterized by determining melting point, $^1$H NMR, $^{13}$C NMR and MALDI-TOF.

In an aspect, the invention provides a process for the synthesis of DTBDT up to gram scale, and the process leads to the desired product with the same yield, purity and other characteristics.

In another aspect, the effect of the ratio of the Grignard reagent used with respect to the amount of 4,8-dehydrobenzo[1,2-b:4,5-b']dithiophene-4,8-dione (BDT) taken was studied for its effect on the yield of DTBDT. BDT: Grignard reagent may be varied between 1:2 to 1:6, preferably 1:4.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Synthesis of (4-(5-(tetramethyl-15-stannyl)thiophen-2-yl)-8-(5-trimethylstannyl) thiophen-2-yl)benzo[1,2-b:4,5-b']dithiophene-2,6-diyl)bis(trimethylstannane) (I)

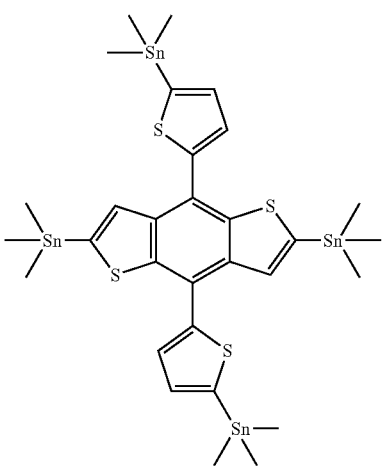

To a solution of 400 mg (10 mmol) of 4,8-di(thiophen-2-yl)benzo[1,2-b:4,5-b']dithiophene in 15 mL of dry THF under argon at −78° C., was added 2.67 ml (1.9M, 42 mmol) of t-butyl lithium drop wise. The reaction mixture was warmed at rt for 2 h, cooled to 0° C., followed by addition of 1.01 g (42 mmol) of trimethyltin chloride in THF (1M) dropwise. The mixture was warmed to room temperature.

After 24 h, the reaction mixture was quenched with water, extracted with Diethyl ether and washed with water three times. The organic phase was dried with sodium sulfate and the solvents were removed under reduced pressure to give crude product. Recrystallization from hexane gave monomer I as a yellow crystal. (953 mg, 84% yield).

$^1$H NMR (500 MHz, CDCl$_3$, ppm): δ 7.70 (s, 2H), 7.66 (d, J=3.11 Hz, 2H), 7.34-7.40 (m, 2H), 0.42 (m, 18H), 0.48 (m, 18H); $^{13}$C NMR (125 MHz, CDCl$_3$, ppm): δ 146.30, 143.16, 142.24, 138.72, 137.25, 135.37, 131.21, 129.04, 122.34, −8.03, −8.31; MALDI-TOF/TOF-MS (in DHB matrix): m/z=1005.6575 [M], calcd. for C$_{30}$H$_{42}$S$_4$Sn$_4$: 1005.7460.

Example 2: General Procedure for the Synthesis of SCOF P1

Under the protection of Argon atmosphere in a sealed tube, monomer I (1 mmol) was dissolved in 2 mL dried toluene, 2,5-dibromo-3,4-dibutylthiophene (2 mmol) dissolved in 2 ml dried toluene was added to the reaction mixture. The solution was degassed with argon for 10 min, and then 10 mol % of Pd (PPh$_3$)$_4$ were added. After that did the freeze thaw cycles 3 times, the reactant was heated to 110° C. for 72 h. The reaction solution was cooled to room temperature, then 2-bromothiophene and trimethyl(thiophen-2-yl) stannane was added as an end capping group. Further reaction mixture was heated to 110° C. for 12 h.

Example 3: General Procedure for the Synthesis of SCOF P2 to P7

Under the protection of Argon atmosphere in a sealed tube, monomer I (1 mmol) was dissolved in 2 mL dried toluene, X—Ar—X (2 mmol) dissolved in 2 ml dried toluene was added to the reaction mixture. The solution was degassed with argon for 10 min, and then 10 mol % of Pd (PPh$_3$)$_4$ were added. After that did the freeze thaw cycles 3 times, the reactant was heated to 110° C. for 72 h. The reaction solution was cooled to room temperature, then 2-bromothiophene and trimethyl(thiophen-2-yl) stannane was added as an end capping group. Further reaction mixture was heated to 110° C. for 12 h.

The reaction mixture cooled to room temperature and then passed through celite pad washed with dichloromethane. Then solution was concentrated on rotary evaporator to remove the solvent. Again dissolved crude reaction mixture in minimum amount of dichloromethane and then added methanol drop wised, formed precipitate filter through whatmann filter paper. The crude product subjected to Soxhlet extraction with pet ether, ethyl acetate and chloroform. The polymer was recovered from chloroform fraction, and the fraction was precipitated into methanol to afford the product solid (82 to 96% yield), P1 to P7 respectively.

The electrochemical and optical properties of synthesized polymers are shown below in Table 2.

TABLE 2

| Polymer | HOMO (ev) | LUMO (ev) | E$_g$ (ev) | λ$_{max}$ (nm) | λ$_{onset}$ (nm) | E$_g$ (from UV) (ev) |
|---|---|---|---|---|---|---|
| P1 | 5.89 | 3.15 | 2.74 | 427 | 549 | 2.26 |
| P2 | 5.93 | 3.85 | 2.08 | 429 | 557 | 2.23 |
| P3 | 4.88 | 3.68 | 1.2 | 343 | 502 | 2.47 |
| P4 | 5.89 | 3.92 | 1.97 | 379 | 530 | 2.34 |
| P5 | 6.07 | 3.71 | 2.36 | 361 | 527 | 2.36 |
| P6 | 5.09 | 3.26 | 1.83 | 382 | 680 | 1.83 |

Example 4: Synthesis of 4,8-Di(thien-2'-yl)-benzo[1,2-b:4,5-b']dithiophene

A solution of 2.96 g (18.16 mmol) of 2-bromothiophene in 40 mL of dry THF was added dropwise to a suspension of 0.45 g (18.16 mmol) of magnesium and I$_2$ (cat.) in 10 mL of dry THF at 0° C. The Grignard reagent was refluxed for 1 hours up to complete Mg dissolved. Subsequently, 4,8-dehydrobenzo[1,2-b:4,5-b']dithiophene-4,8-dione (1.0 g, 4.54 mmol) was quickly added, and the reaction mixture was stirred at 50° C. for 6 hours. Then the reaction mixture was cooled to ambient temperature. A solution of SnCl$_2$ (8.2 g, 36.3 mmol) in 10% HCl (10 mL) was then added. The reaction mixture was stirred for an additional 1.5 hours and poured into ice water. The mixture was extracted twice with petroleum ether. The organic phase was dried over Na$_2$SO$_4$ and concentrated. The crude product was purified by silica gel chromatography using petroleum ether as the eluent to yield the pure product as a yellow solid (1.08 g, yield 67%).

m.p. 207-210° C.; $^1$H NMR (500 MHz, CDCl$_3$, ppm): δ 7.59 (d, J=5.7 Hz, 2H), 7.53-7.54 (m, 2H), 7.49-7.50 (m, 2H), 7.46 (d, J=5.7 Hz, 2H), 7.25-7.26 (m, 2H); $^{13}$C NMR (125 MHz, CDCl$_3$, ppm): δ 139.60, 139.24, 136.72, 128.05, 127.77, 127.42, 126.40, 123.86, 123.22; MALDI-TOF/TOF-MS: m/z=353.882 [M]+, calcd. for C$_{18}$H$_{10}$S$_4$: 353.9660.

Example 5: Effect of the Quantity of Bromothiophene

The effect of the quantity of Bromothiophene Grignard used on the yield of the final product, DTBDT, was studied and the results are tabulated o in Table 3. The process followed was as enlisted in example 1.

TABLE 3

Effect of the quantity of Bromothiophene Grignard used on the yield of the final product:

| Sr. No. | BDT | 2-Bromothiophene Grignard | % of Product |
|---|---|---|---|
| 1. | 1 eq | 2.2 eq | 45 |
| 2. | 1 eq | 4.0 eq | 67 |
| 3. | 1 eq | 6.0 eq | 68 |

When 2.2 equivalent of 2-Bromothiophene Grignard with respect to BDT was used 45% yield of DTBDT was observed. By increasing the equivalents of Grignard reagent up to 4 equivalents the yield was improved to 67%. However further increase in Grignard reagent amount to six equivalences, no improvement in yield was observed.

ADVANTAGES OF INVENTION a. Novel compound and its polymer.

b. One pot synthesis of 4,8-di(thiophen-2-yl)benzo[1,2-b:4,5-b']dithiophene.

c. Applications in organic photovoltaics.

d. Polymers can be used to build devices for capacitor and solar applications.

e. One pot process
f. Standardized up to gm scale
g. Process provides good yields
The invention claimed is:
1. A polymer of formula (II):
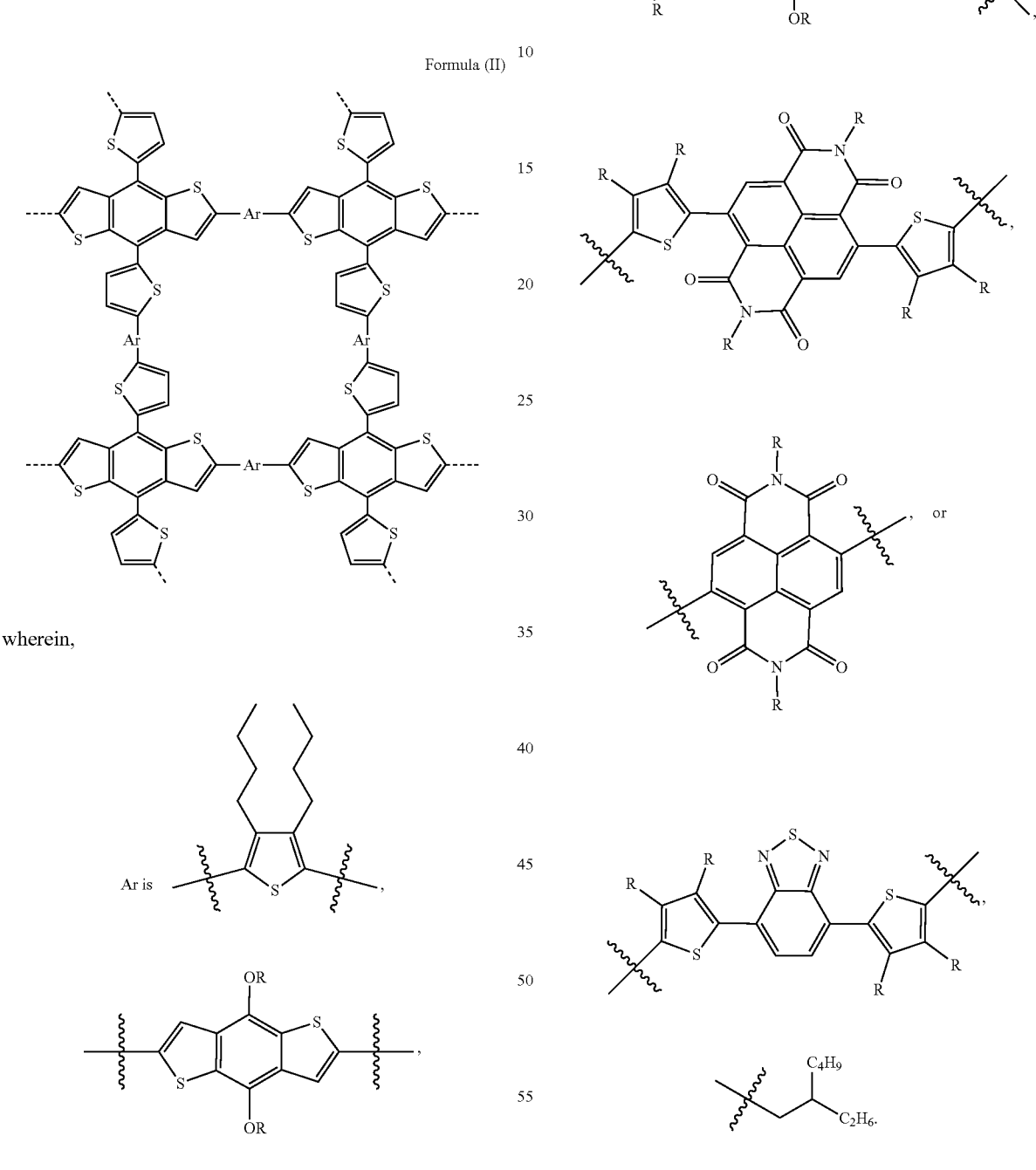
Formula (II)
wherein,
Ar is 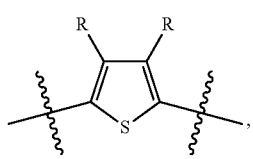,
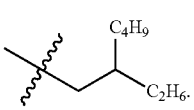
in which R is

2. The polymer as claimed in claim 1, wherein the polymer is
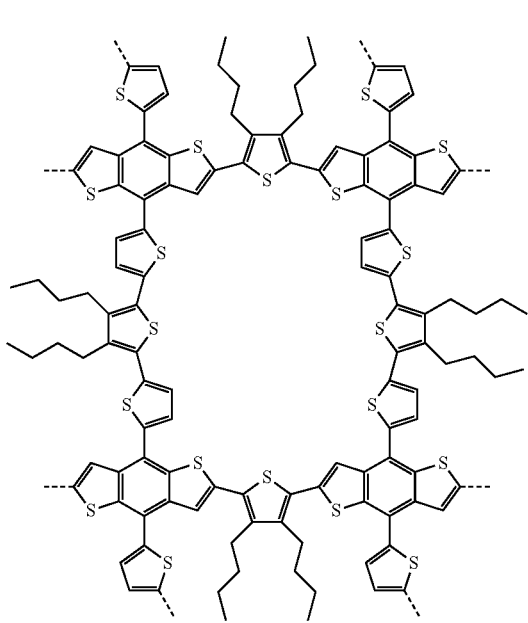
3. The polymer of claim 1, wherein the polymer is
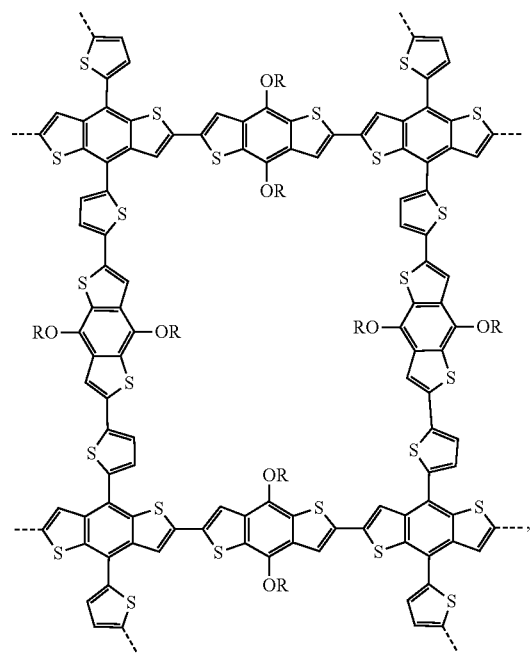
in which R is
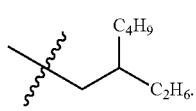
4. The polymer of claim 1, wherein the polymer is
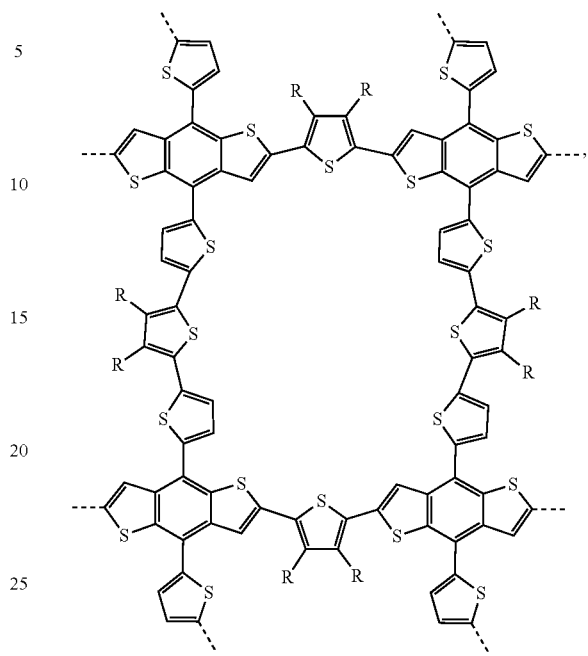
in which R is
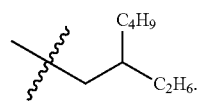
5. The polymer of claim 1, wherein the polymer is
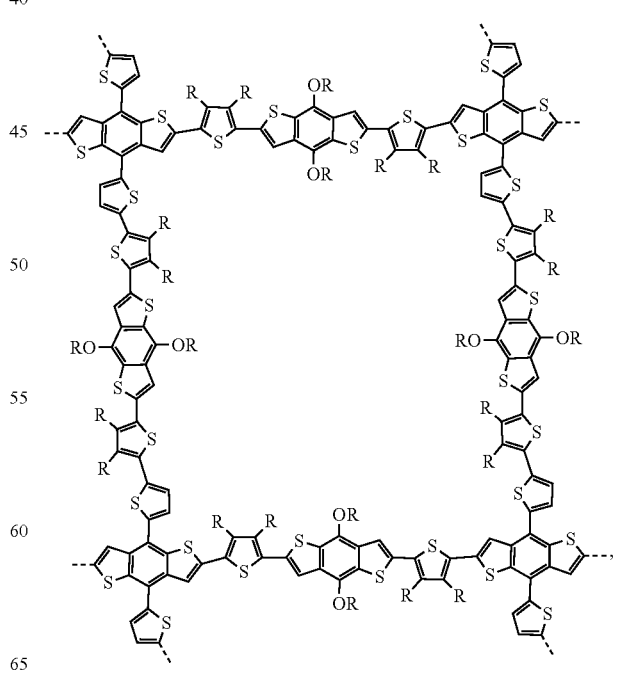

in which R is
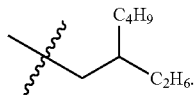
6. The polymer of claim 1, wherein the polymer is
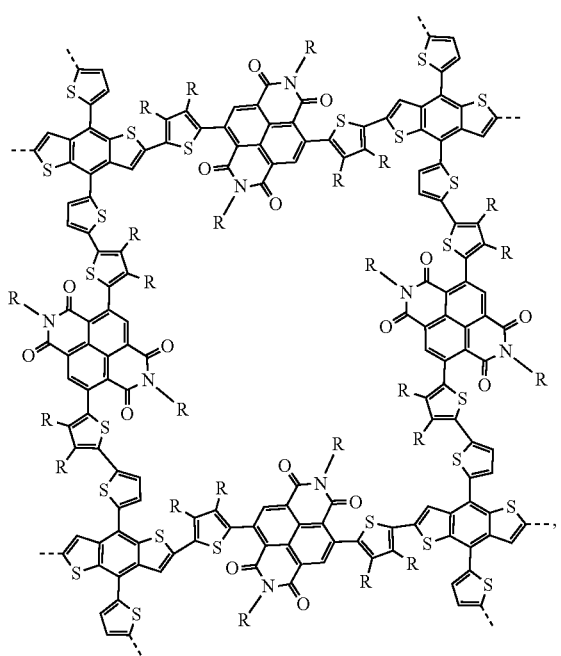
in which R is
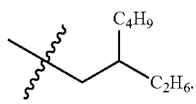
7. The polymer of claim 1, wherein the polymer is
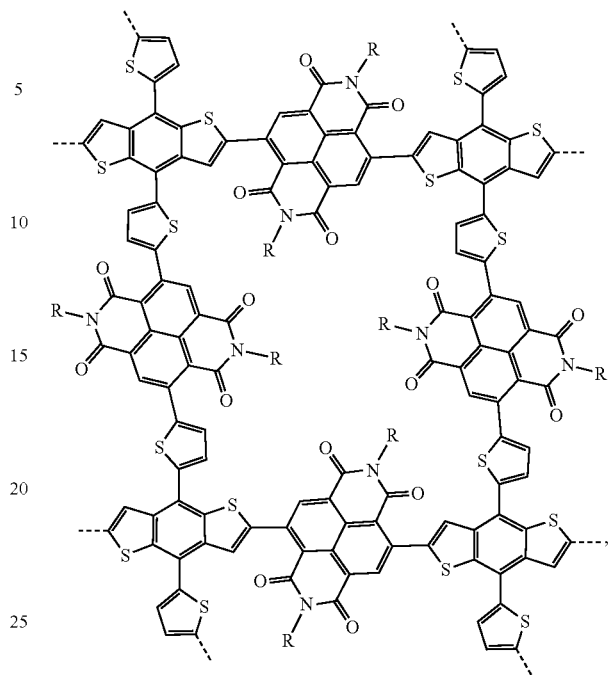
in which R is
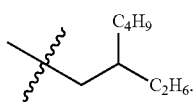
8. The polymer of claim 1, wherein the polymer is
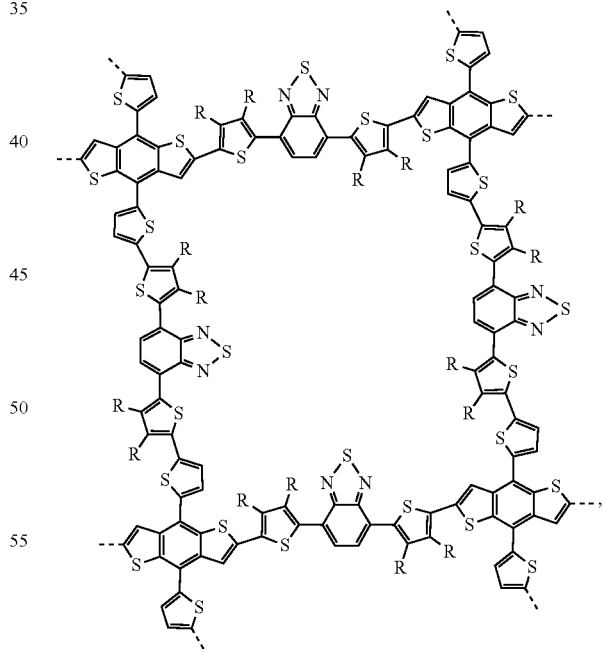
in which R is
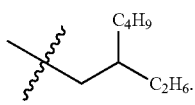

9. A process for the synthesis of the polymer of formula (II) of claim 1, wherein the process comprises the steps of:
dissolving a monomer of formula (I) and Br—Ar—Br in a solvent to obtain a first reaction mixture:

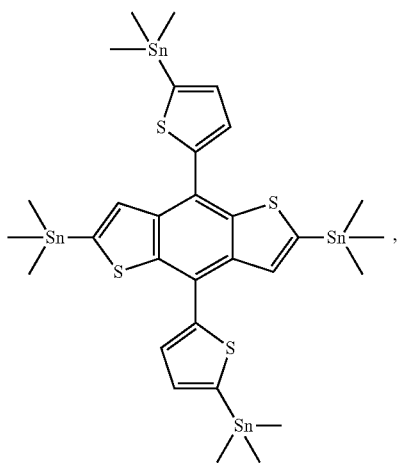

Formula (I)

in which Ar is defined in claim 1 and Br is a bromide group;

degassing the first reaction mixture of step (a) and adding tetrakis(triphenylphosphine)palladium £Pd(PPh$_3$)$_4$) to the first reaction mixture to form a second reaction mixture, followed by heating the second reaction mixture at a temperature in the range of 100 to 110° C. for a period in the range of 70 to 74 hours;

adding 2-bromothiophene and trimethyl(thiophen-2-yl) stannane to the second reaction mixture to form a third reaction mixture, followed by heating the third reaction mixture at a temperature in the range of 100 to 110° C. for a period in the range of 10 to 14 hours to produce with the polymer of formula (II).

10. The process as claimed in claim 9, wherein said solvent is toluene.

* * * * *